US008673614B2

(12) United States Patent
Lorah et al.

(10) Patent No.: US 8,673,614 B2
(45) Date of Patent: *Mar. 18, 2014

(54) ANAEROBIC MICROBIAL COMPOSITION AND METHODS OF USING SAME

(75) Inventors: Michelle M. Lorah, Finksburg, MD (US); Elizabeth J. Jones, Manassas, VA (US); Mary A. Voytek, Arlington, VA (US)

(73) Assignee: The United States of Amerivca as represeted by the Secretary of the Army, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/299,382

(22) Filed: Nov. 18, 2011

(65) Prior Publication Data

US 2012/0064605 A1 Mar. 15, 2012

Related U.S. Application Data

(62) Division of application No. 12/131,666, filed on Jun. 2, 2008, now Pat. No. 8,105,808.

(60) Provisional application No. 60/936,017, filed on Jun. 13, 2007.

(51) Int. Cl.
  *C12N 1/20* (2006.01)
  *C12Q 1/68* (2006.01)
  *C12P 7/00* (2006.01)
  *C07H 21/04* (2006.01)
  *C07H 21/02* (2006.01)
  *C12N 1/00* (2006.01)

(52) U.S. Cl.
  USPC ......... 435/243; 435/252.3; 435/6.1; 435/132; 536/23.2; 536/23.1

(58) Field of Classification Search
  None
  See application file for complete search history.

(56) References Cited

U.S. PATENT DOCUMENTS

| 6,503,746 | B1 | 1/2003 | Daane et al. |
| 6,783,678 | B2 | 8/2004 | Sorenson |
| 6,946,248 | B2 | 9/2005 | Sowers et al. |
| 2002/0015991 | A1 | 2/2002 | Brennan et al. |
| 2006/0194303 | A1 | 8/2006 | DeWitt et al. |
| 2006/0223160 | A1 | 10/2006 | Vanzin |

OTHER PUBLICATIONS

Jones, Elizabeth J. P., et al., "Characterization of a Microbial Consortium Capable of Rapid and Simultaneous Dechlorination of 1,1,2,2-Tetrachloroethane and Chlorinated Ethane and Ethene Intermediates," Bioremediation Journal, 2006, p. 153-168, vol. 10.
Jones, M.M., et al., "Biostimulation and Bioaugmentation to Enhance Degradation of Chlorinated Solvents in Wetland Sediments," In Situ and On-Site Bioremediation, 2003.
Tiedje, James M., et al., "Aerobic and Anaerobic Transformation of cis-Dichloroethene (cis-DCE) and Vinyl Chloride (VC): Steps for Reliable Remediation," Final Technical Report CU-1167, Dec. 2003.
GeoSyntec Consultants, "Bioaugmentation for Remediation of Chlorinated Solvents: Technology Development, Status, and Research Needs," Oct. 2005.
Washington Savannah River Company, "Enhancements to Natural Attenuation: Selected Case Studies," May 2007, WSRC-STI-2007-00250.
Jones, Elizabeth, J. P., et al., "Development and Composition of a Mixed Culture for Bioremediation of Chlorinated Ethenes and Ethanes," In Situ and On-Site Bioremediation, Jun. 2005.
Lorah, Michelle, et al., "Physiological Characterization of a Broad Spectrum Reductively Dechlorinating Consortium," In Situ and On-Site Bioremediation, Jun. 2005.
Lorah, Michelle, et al., "Electron Donor Preference of a Reductive Dechlorinating Consortium," In Situ and On-Site Bioremediation, Jun. 2005.
Majcher, Emily H., "Design and Installation of an Innovative Enhanced Bioremedation Pilot Test in a Tidal Wetland," In Situ and On-Site Bioremediation, Jun. 2005.

*Primary Examiner* — Yong Pak
(74) *Attorney, Agent, or Firm* — Elizabeth Arwine

(57) ABSTRACT

A microbial composition for concurrent dechlorination of a mixture of chlorinated ethanes and chlorinated ethenes includes a isolated consortium of bioremediative microorganisms comprising strains of microorganism comprising *Clostridium, Acetobacterium, Dehalobacter, Bacteroides,* and Proteobacteria. The composition may also include Methanomicrobia.

13 Claims, 9 Drawing Sheets

ANAEROBIC MICROBIAL COMPOSITION AND METHODS OF USING SAME

This application is a divisional application of U.S. Ser. No. 12/131,666 filed on Jun. 2, 2008 which claims priority of provisional patent application Ser. No. 60/936,017 filed on Jun. 13, 2007, the entireties of which are incorporated herein by reference.

I. FIELD OF THE INVENTION

The present invention relates to an anaerobic microbial composition and to methods of using the microbial composition for effectively dechlorinating at least one of chlorinated ethanes, chlorinated ethenes, chlorinated methanes, or mixtures thereof.

II. BACKGROUND OF THE INVENTION

Bioaugmentation (site inoculation with a microbial culture) is a proven approach for stimulating complete dechlorination of sites contaminated with chlorinated ethenes. However, cultures have not been available for the large-scale treatment of chlorinated ethane contamination. Of additional concern, chlorinated ethanes can inhibit the degradation of chlorinated ethenes. Thus, cultures are needed for bioremediation of sites with mixtures of these contaminants.

Contamination of groundwater with chlorinated ethenes and ethanes is a serious problem due to widespread and historic commercial, industrial, and military use, relative resistance to degradation, and associated health hazards. Under anaerobic conditions, chlorinated ethenes and ethanes can be partially reduced to less chlorinated compounds or completely degraded to nonchlorinated end products depending on the physiological capability of an indigenous microbial community.

Bacterial isolates capable of reducing 1,2-dichloroethane (DCA) and 1,1,1-trichloroethane have been identified. One isolate has been shown to reduce 1,1,2,2-tetrachloroethane (TeCA) to cis 1,2-dichloroethene (cisDCE). Recent research on a mixed culture demonstrated growth of *Dehalobacter* sp. with the reduction of 1,1,2-trichloroethane (TCA) to vinyl chloride (VC). See Jones et al., *Characterization of a Microbial Consortium Capable of Rapid and Simultaneous Dechlorination of 1,1,2,2-Tetrachloroethane and Chlorinated Ethane and Ethene Intermediates*, Bioremediation Journal, 10:153-168 (2006), the disclosure of which is incorporated herein by reference in its entirety.

III. SUMMARY OF INVENTION

According to an aspect of the invention, a composition is provided for concurrent dechlorination of a mixture of chlorinated ethanes and chlorinated ethenes. The composition includes an isolated bioremediative consortium comprising strains of microorganism comprising *Clostridium, Acetobacter, Dehalobacter, Bacteroides*, and Proteobacteria.

According to another aspect of the invention, a composition is provided for concurrent dechlorination of a mixture of chlorinated ethanes and chlorinated ethenes. The composition includes a non-naturally occurring consortium of dechlorinatingly effective microbial species. The consortium of effective dechlorinatingly microbial species comprises at least one 16S rDNA nucleic acid sequence that has more than 95% identity to a nucleic acid sequence consisting of SEQ ID NO 1, a nucleic acid sequence consisting of SEQ ID NO 2, or a nucleic acid sequence consisting of SEQ ID NO 3.

According to another aspect of the invention, a method for dechlorinating chlorinated waste is provided including contacting at least one of chlorinated ethanes, chlorinate ethenes, or chlorinated methanes with an isolated bioremediative consortium comprising strains of microorganism comprising Clostridiales, Cytophaga-flavobacterium-bacterioides, Proteobacteria, and Methanomicrobia; and anaerobically dechlorinating the at least one of chlorinated ethanes, chlorinate ethenes or chlorinated methanes.

According to another aspect of the invention, a method of producing a microbial consortium comprises culturing microbes of a sediment sample obtained from a site contaminated with a mixture of chlorinated ethanes and chlorinated ethenes in an anaerobic medium with at least one chlorinated ethane and an electron donor.

IV. BRIEF DESCRIPTION OF THE DRAWINGS

V. DETAILED DESCRIPTION OF INVENTION

The present invention is directed to an anaerobic microbial composition or consortium comprising bioremediative organisms. The invention is also directed to methods of using the microbial composition for the effective dechlorination of at least one of chlorinated ethanes, chlorinated ethenes, chlorinated methanes, or mixtures thereof. The consortium of the present invention may be employed for bioremediation to anaerobically biodegrade chlorinated waste, for example, contaminated groundwater or contaminated soil from landfill sites, river beds, lakes, wetlands, and the like.

Figure 1:
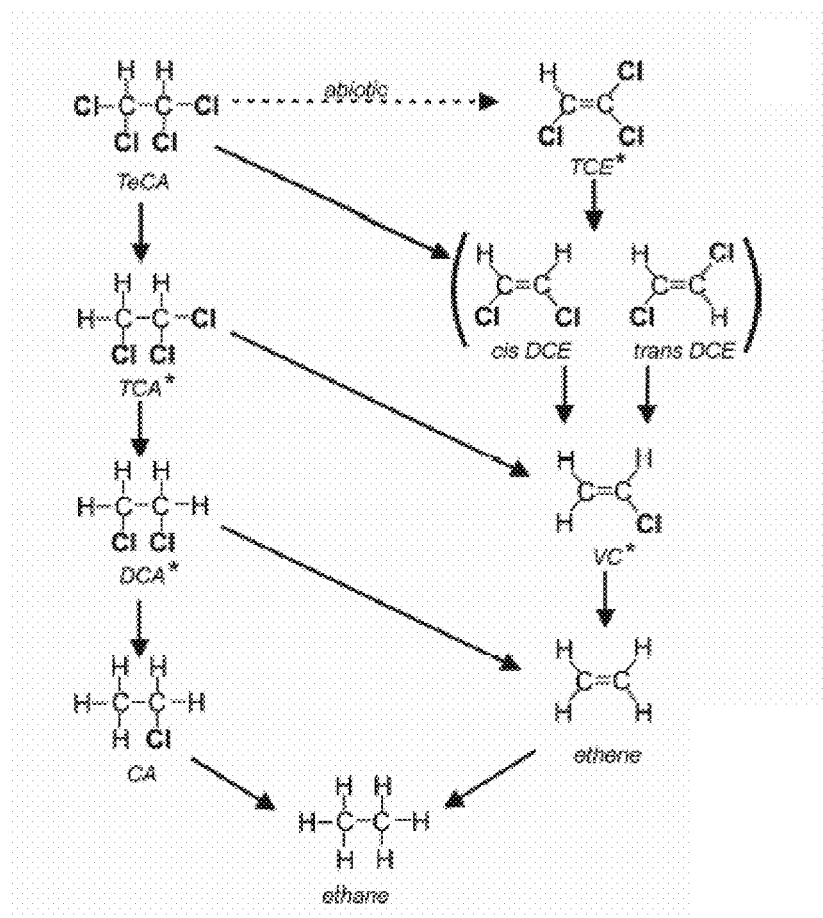
FIG. 1 illustrates possible pathways of anaerobic 1,1,2,2-tetrachloroethane (TeCA) dechlorination. Compounds for which the EPA reports an increased risk of cancer are indicated with an asterisk.

FIG. 1 illustrates that the TeCA degradation pathway is primarily biotic and includes both hydrogenolysis to less chlorinated ethanes and dichloroelimination to less chlorinated ethenes. Abiotic production includes the production of trichloroethene (TCE) from dehydrochlorination of TeCA.

Several intermediates of TeCA dechlorination are possible carcinogens and are listed as contaminants of concern by the U.S. Environmental Protection Agency. VC is a known human carcinogen that often accumulates at sites where dechlorination is slow or incomplete.

Natural attenuation of TeCA has been documented at Aberdeen Proving Ground (APG) in Maryland, where contaminated groundwater discharges through anoxic wetland sediments at West Branch Canal Creek. Chloroethane (CA), ethene and ethane have not been observed in the sediment. According to the present invention, a microbial consortium, West Branch Consortium (WBC-2), was derived from organic-rich sediments collected in the wetland of West Branch Canal Creek at APG. As disclosed below, WBC-2 can dechlorinate chlorinated ethanes and chlorinated ethenes, both individually and concurrently.

According to an embodiment of the present invention, a microbial composition, WBC-2, for concurrent dechlorination of a mixture of chlorinated ethanes and chlorinated ethenes, comprises an isolated bioremediative consortium comprising strains of microorganism comprising *Clostridium, Acetobacter, Dehalobacter, Bacteroides*, and Proteobacteria. The microbial composition may also comprise Methanomicrobia, for example, at least one of *Methanosarcina* or *Methanosaeta*. The consortium may comprise *Dehalococcoides*.

In embodiments, the microbial composition may comprise a non-naturally occurring consortium of dechlorinatingly effective microbial species comprises at least one 16S rDNA nucleic acid sequence that has more than 95% identity to a nucleic acid sequence consisting of SEQ ID NO 1, a nucleic acid sequence consisting of SEQ ID NO 2, or a nucleic acid sequence consisting of SEQ ID NO 3. In embodiments, the consortium may comprise at least one 16S rDNA a nucleic acid sequence that has more than 95% identity to a nucleic acid sequence consisting of SEQ ID NO 4 or SEQ ID NO 5. In embodiments, the consortium may comprise at least one 16S rDNA a nucleic acid sequence that has more than 95% identity to a nucleic acid sequence consisting of SEQ ID NO 6 or SEQ ID NO 7.

In embodiments, the microbial composition may comprise at least one methyl coenzyme-M reductase nucleic acid sequence that has more than 95% identity to a nucleic acid sequence consisting of SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, or SEQ ID NO 20.

According to a method of the present invention, a mixture of chlorinated ethanes and chlorinated ethenes may be dechlorinated by contacting the mixture with a microbial composition of the present invention and concurrently anaerobically dechlorinating the mixture of chlorinated ethanes and chlorinated ethenes. According to an embodiment of the invention, the chlorinated ethanes may comprise at least one of 1,1,2,2-tetrachloroethane; 1,1,2-trichloroethane; 1,2-dichloroethane, or chloroethane. The chlorinated ethenes may comprise at least one of cis 1,2-dichloroethene; trans 1,2-dichloroethene; vinyl chloride; or tetrachloroethene. The mixture may also contain chlorinated methane, for example, carbon tetrachloride or chloroform.

According to a method of the present invention, chlorinated waste may be dechlorinated by contacting at least one of chlorinated ethanes, chlorinate ethenes or chlorinated methanes with an isolated bioremediative consortium comprising strains of microorganism comprising Clostridiales, Cytophaga-flavobacterium-bacterioides, Proteobacteria, and Methanomicrobia; and anaerobically dechlorinating the at least one of chlorinated ethanes, chlorinate ethenes, or chlorinated methanes. The chlorinated waste may comprise contaminated soil or contaminated water.

The microbial consortium according to the present invention may be produced by culturing microbes of a sediment sample obtained from a site contaminated with a mixture of chlorinated ethanes and chlorinated ethenes in an anaerobic medium with at least one chlorinated ethane and an electron donor. In embodiments, the electron donor may be selected from the group consisting of lactate, pyruvate, benzoate, and ethanol.

Example

Properties and Composition of WBC-2 Anaerobic Microbial Composition

A. Dechlorination Properties of WBC-2 Microbial Composition

WBC-2 was cultivated in batches amended with either lactate and TeCA or lactate and a mixture of TeCA, TCA, and cisDCE for 18 months.

Figure 2A:
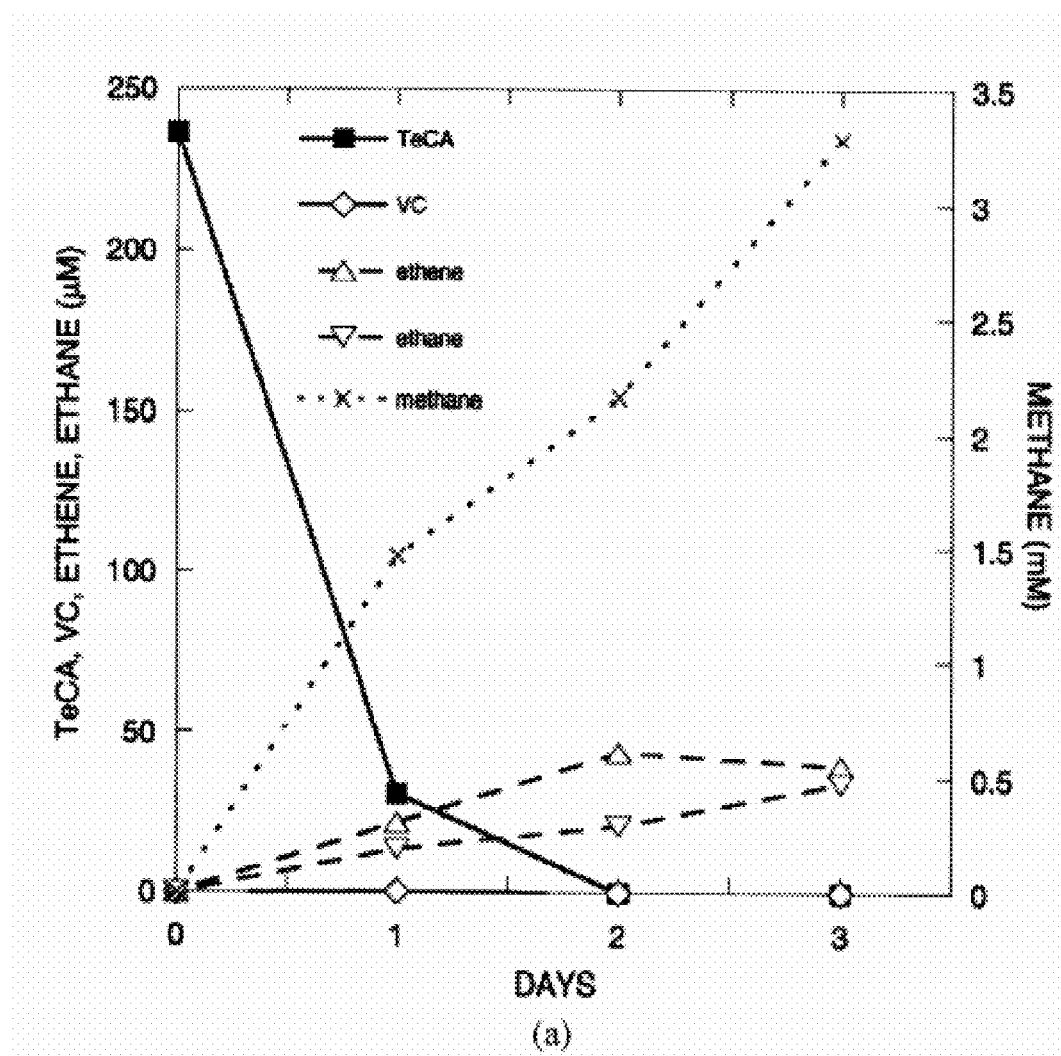
FIGS. 2A-2B illustrate dechlorination in stock microbial cultures according to the present invention amended with lactate and (A) TeCA only or lactate and (B) TeCA, TCA and cisDCE.

In the TeCA amended culture, WBC-2 in a 2 L batch culture completely dechlorinated TeCA (measured at 240 μM) within 2 days, as shown in FIG. 2A. The pathway of TeCA degradation could not be discerned by monitoring this culture because very little intermediate accumulation occurred. Less than 0.5 μM (0.2% of the added TeCA) accumulated as VC, and this VC was degraded by day 2. The end products of dechlorination were ethene and ethane.

Figure 2B:
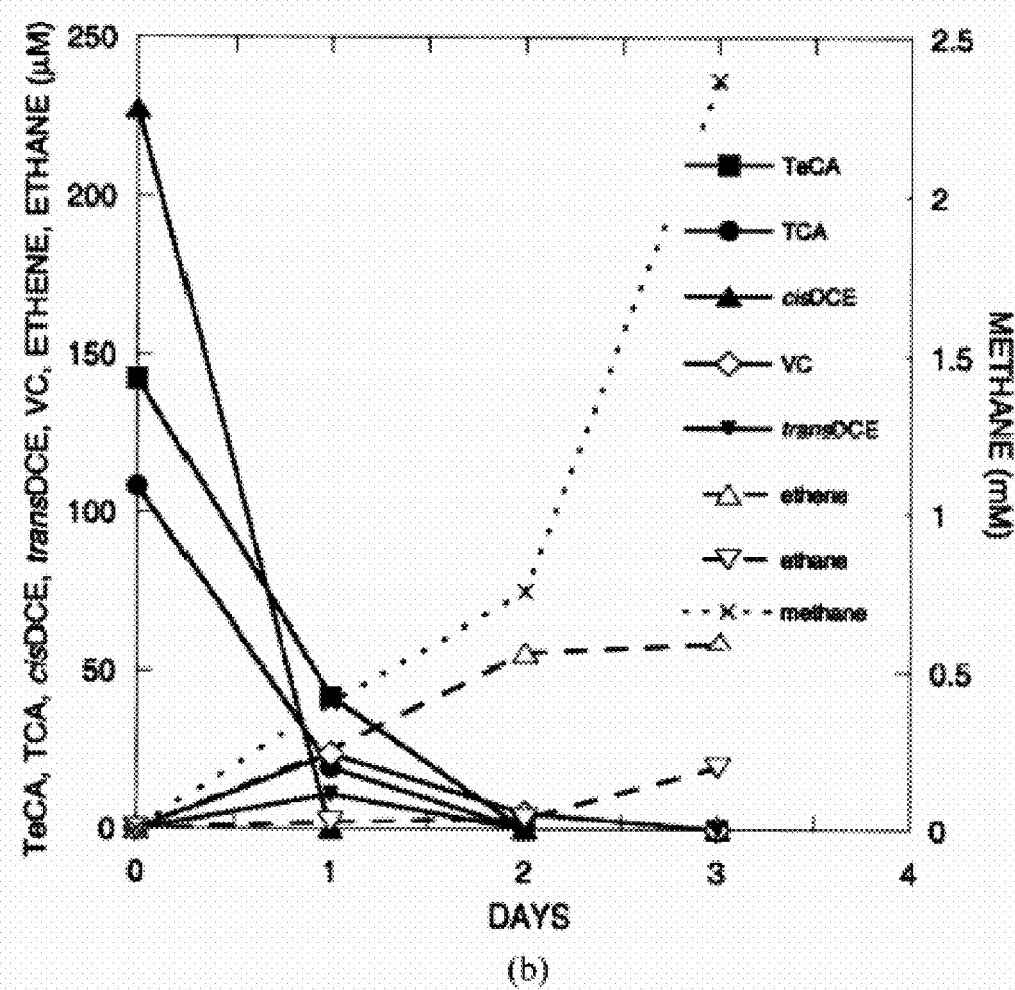

In a 2 L batch culture maintained with the chlorinated mixture (TeCA, TCA, and cisDCE), WBC-2 rapidly, simultaneously, and completely reduced all three chlorinated compounds to the nonchlorinated end-products ethene and ethane, as shown in FIG. 2B. Small amounts of transDCE and VC were observed as transient intermediates.

Figure 3:
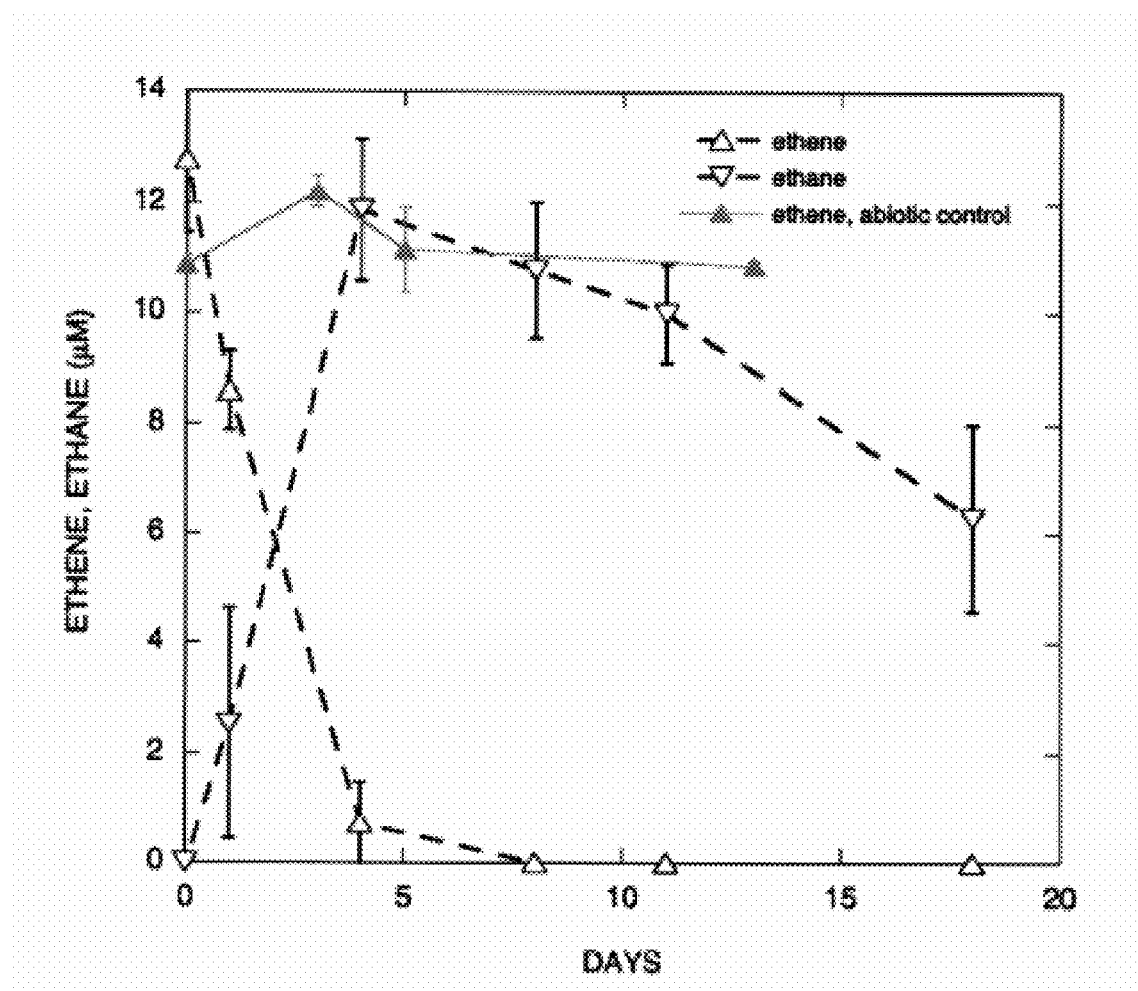
FIG. 3 illustrates degradation of ethene and production of ethane in a microbial culture according to the present invention after depletion of chlorinated compounds.

After dechlorination was complete, the fate of ethene was monitored in the cultures in order to determine if ethene reduction could account for the production of ethane. As shown in FIG. 3, ethene was degraded (6 μM day$^{-1}$) with the production of ethane. After ethene was depleted, the ethane concentration also decreased, at a rate of 0.5 μM day$^{-1}$. The lack of stoichiometric accumulation of ethane suggests that ethane and ethene degradation can co-occur.

Figures 4A, 4B:
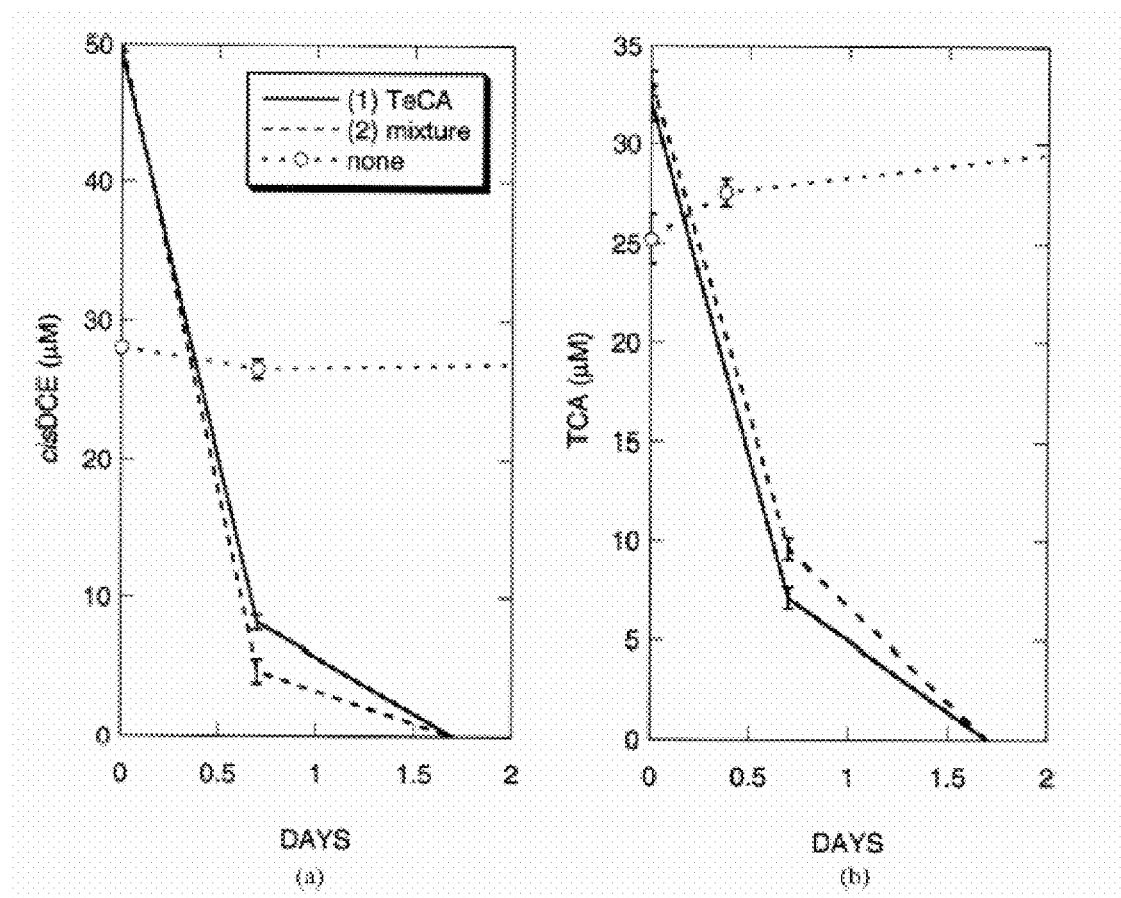
FIGS. 4A-4B illustrate cisDCE (A) and TCA (B) degradation by stock microbial cultures according to the present invention grown with (1) TeCA only and (2) a mixture of TeCA, TCA, and cisDCE, and (3) no culture added.

Pathways of intermediate degradation were determined by incubating sub samples of WBC-2 with TCA or cisDCE. WBC-2 cultures that had been maintained with (1) TeCA and (2) the chlorinated mixture (TeCA, TCA, cisDCE) were incubated to deplete chlorinated compounds and then compared with respect to their capabilities to degrade cisDCE (FIG. 4A) and TCA (FIG. 4B). The two cultures were very similar in their abilities to degrade the two TeCA intermediates.

Figures 5A, 5B:
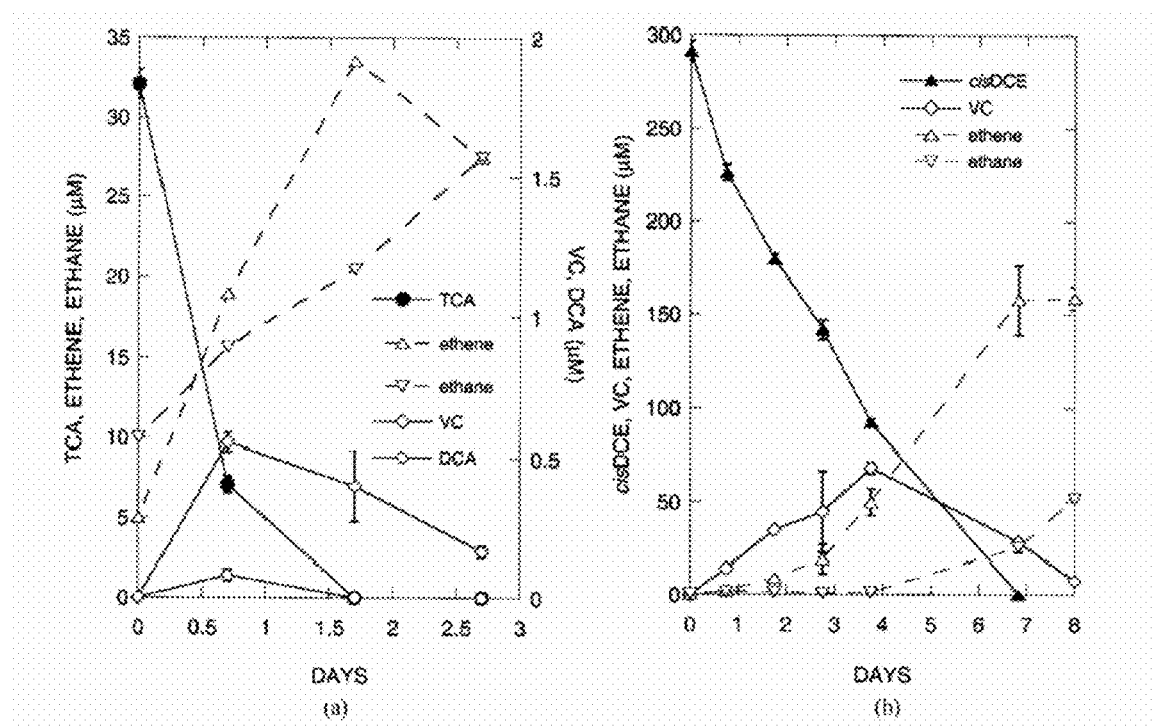
FIGS. 5A-5B illustrate production and degradation of chlorinated intermediates of (A) TCA and (B) cisDCE in a microbial culture according to the present invention.

Degradation products of intermediate dechlorination are shown for TeCA-maintained WBC-2 (FIGS. 5A-5B). Little intermediate accumulation was observed in TCA-amended treatments (FIG. 5A). The rate of TCA degradation was 36 μM day$^{-1}$. The peak VC and DCA concentrations measured were 1.7% and 0.3% of the TCA added, respectively, and both intermediates were rapidly degraded. Chloroethane was not detected. As shown in FIG. 5B, cisDCE reduction was accompanied by the production of VC (peak accumulation, 24% of added cisDCE), ethene and ethane. The rate of cisDCE degradation in cultures amended with cisDCE was 54 μM day$^{-1}$.

Figures 6A, 6B:
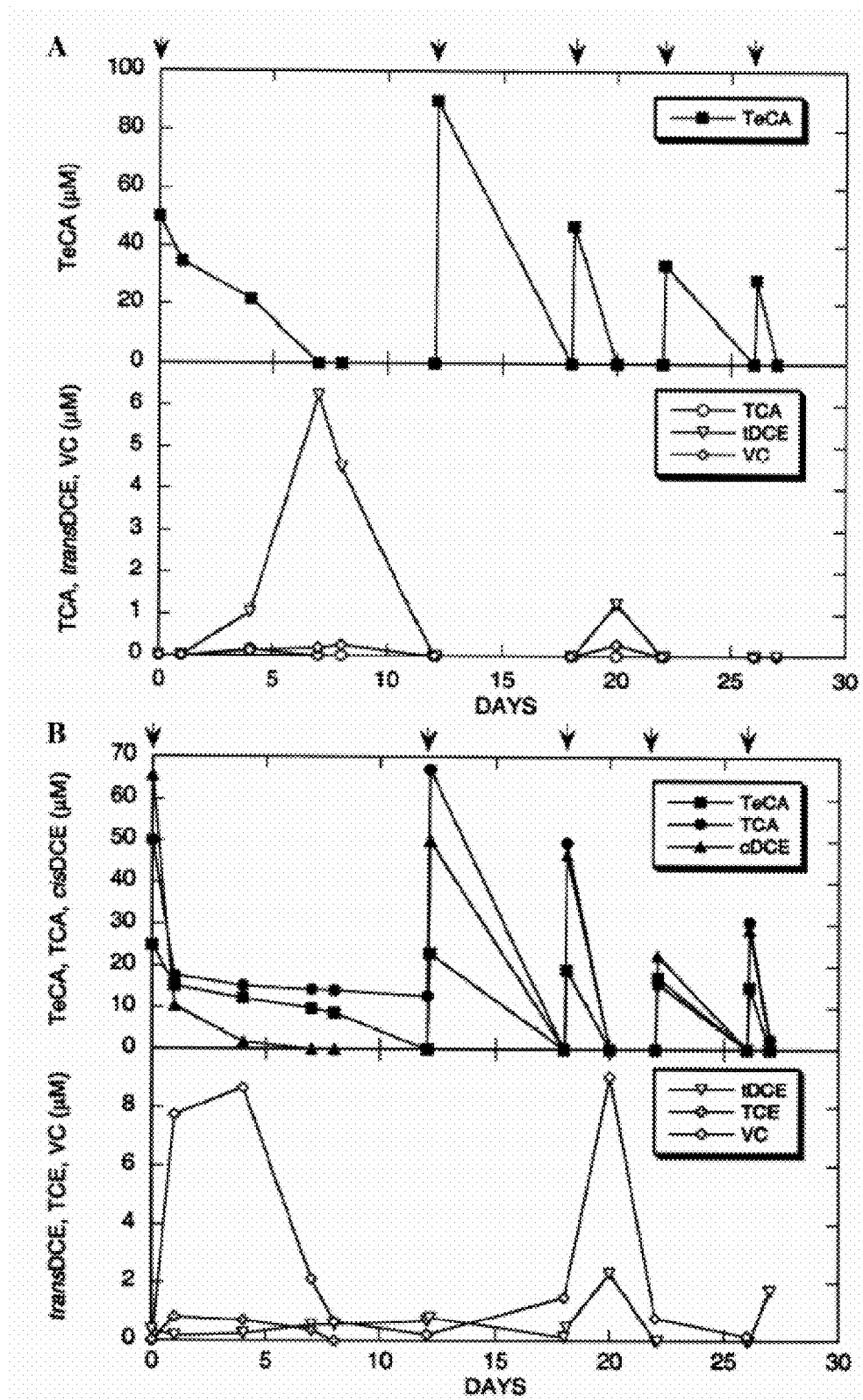
FIGS. 6A-6B illustrate dechlorination of added compounds and accumulation of intermediates in cultures transferred to fresh medium and amended with lactate and either (A) TeCA only or (B) TeCA, TCA, and cisDCE.

When WBC-2 cultures were diluted (1:9) into fresh medium, dechlorination was initially slow enough to allow the observation of intermediates. As shown in FIG. 6A, diluted cultures amended with lactate and TeCA (as shown by arrows) accumulated measurable TCA (0.01 μM) at one time point, and transDCE (6 μM) and VC (0.25 μM) were also both produced and degraded.

As shown in FIG. 6B, diluted cultures amended with TeCA, TCA, and cisDCE (as shown by arrows) had a transient accumulation of VC (6% of the added chlorinated compounds) and transDCE (as much as 4% of added TeCA), and also the abiotic product, TCE (3% of the TeCA parent added). Within 2 to 4 weeks, dechlorination rates increased to a level comparable to that observed in undiluted cultures, with parent compounds degraded in as little as one day and little transient accumulation of intermediates.

After microbial enrichment and 1 year in culture, the rates of WBC-2 dechlorination for TeCA, TCA, and cisDCE were 100, 36, and 54 μM day$^{-1}$, respectively. Almost no intermediates were detected in WBC-2 cultures amended with TeCA or a mixture of TeCA, TCA, and cisDCE. Although intermediates often did not accumulate, the ability of WBC-2 to degrade all known intermediates in the TeCA pathway was demonstrated in treatments with individual compounds (e.g., TCA and cisDCE) and in mixtures (e.g., TeCA, TCA, cisDCE). Ethene and ethane are major products of TeCA degradation.

The unique contribution of WBC-2 for contaminant treatment is the ability of the microbial composition to handle a variety of compounds (both chlorinated ethenes and ethanes) without noticeable inhibition. WBC-2 also has the ability to degrade chlorinated ethenes and ethanes simultaneously. WBC-2 is also able to reduce tetrachloroethene (PCE) in the presence of TeCA.

WBC-2 also has other properties regarding sensitivity to pH, oxygen, and chlorinated methanes.

Batch microcosms were conducted under anaerobic conditions in culture medium with neutral pH and with pH adjusted from acidic (pH 4, 5, and 6) to alkaline (pH 8 and 9). The ability of the WBC-2 consortium to fully dechlorinate chlorinated ethanes and ethenes was evaluated for each pH-adjusted treatment. The WBC-2 consortium was intolerant of acidic conditions of pH 5 and lower, resulting in a loss of dechlorinating ability. The consortium was tolerant of alkaline pH with no apparent loss of activity.

Reductive dechlorinating organisms commonly have high negative sensitivity to oxygen exposure over short time-frames, which complicates their field application. To evaluate oxygen sensitivity of WBC-2, an aliquot was removed from an anaerobic culture vessel and poured into smaller containers on the bench top where a series of oxygen exposures were applied to the culture by bubbling ambient air through the culture at a rate of approximately 100 milliliters per minute. Following time exposures of 1, 5, 20, and 60 minutes, each treatment was purged with anaerobic gas, sealed, and amended with 1,1,2,2-tetrachloroethane, 1,1,2-trichloroethane, and cis-1,2-dichloroethene, and an electron donor. Treatments were monitored for dechlorinating for 11 days or until complete dechlorination was observed. Dechlorinating activity was observed to be comparable to the culture with no exposure to oxygen up to an exposure time of 20 minutes. After 60 minutes of exposure, dechlorination activity was partially inhibited but eventually continued to completion during incubation under strict anaerobic conditions.

Chlorinated methanes tend to inhibit the activity of a wide range of organisms. To test the sensitivity of WBC-2 to carbon tetrachloride (CT), a series of batch experiments in culture medium were conducted along with flow-through column experiments with a bioaugmented, wetland-like, organic matrix. Although toxicity effects from CT addition were observed with WBC-2 in liquid culture at a concentration of 3 mg/L, WBC-2 in the columns could maintain degradation of CT and chloroform (CF) and of the chlorinated ethanes and ethenes at CT and CF concentrations of 10 and 20 mg/L, respectively.

B. Composition of the WBC-2 Microbial Composition

Figures 7A, 7B, 7C, 7D:
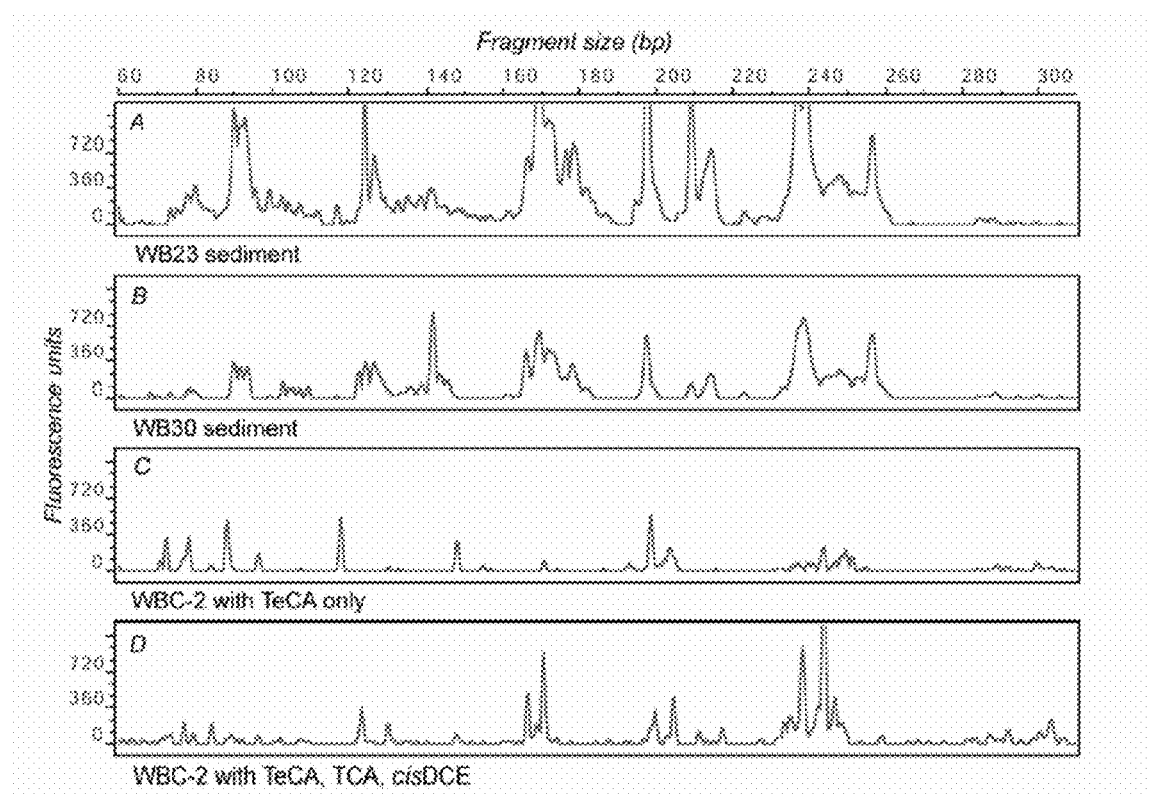
FIGS. 7A-7D illustrate a comparison of TRFLP profiles for APG sediments WB23 (A) and WB30 (B), and for a microbial composition according to the present invention after 1 year in culture with TeCA (C) or a mixture of chlorinated compounds (D).

As shown in FIGS. 7A-7D, the bacterial community in the source APG sediments (WB23, FIG. 7A; WB30, FIG. 7B) shifted after a year under culture conditions with lactate as the electron donor and TeCA (FIG. 7C) or a mixture of TeCA, TCA, and cisDCE (FIG. 7D) as electron acceptors.

Both WBC-2 cultures (cultured with TeCA as shown in FIG. 7C or TeCA, TCA, and cisDCE as shown in FIG. 7D) exhibited TRFLP profiles that were different from that of the source sediments and overall represented a different community than was present in the starting materials. This change reflects the selection pressures exerted on the community and individual members by the chlorinated compounds, such that the remaining peaks represent members tolerant of the chlorinated compounds and favored by the culturing conditions and perhaps directly or indirectly involved in the degradation process.

The numerically dominant phylogenetic types in WBC-2 were identified by cloning and sequencing 16S rDNA and mcrA genes from a culture grown with a mixture of TeCA, TCA, and cisDCE. The frequency of phylotype occurrence in 16S rDNA clone libraries and mcrA clone libraries, and phylogenetic placement was determined using a BLAST search for related sequences.

Although most of the WBC-2 clones were not related to dechlorinating bacteria that have been studied in isolation, many were related to bacterial clones that have been observed at other dechlorinating sites, as shown in Table 2:

TABLE 2

Frequency of WBC-2 Clones and Their Closest BLAST Matches to a Dechlorinating Isolate or to Clone Sequences from a Dechlorinating Environment

| Phylotype frequency | Phylogenetic placement | Clone id | BLAST hits[1] (% similiar) | Source |
|---|---|---|---|---|
| 48/133 | *Clostridium* | acc #DQ907197 | *AY667266 (99%) | TCE-dechlorinating community |
| 35/133 | Acetobacteria | acc #DQ907202 | *AY185312 (97%) AY185315 (97%) AY185311 (96%) | 1,2-Dichloropropane-dechlorinating enrichment |
| 2/133 | *Dehalobacter* | acc #DQ907207 | *AF422637 (95%) AY754830 (93%) DQ663785 (93%) | TCE-reducing community PCB-dechlorinating culture 111-trichloroethane degrading mixed culture |

TABLE 2-continued

Frequency of WBC-2 Clones and Their Closest BLAST Matches to a Dechlorinating Isolate or to Clone Sequences from a Dechlorinating Environment

| Phylotype frequency | Phylogenetic placement | Clone id | BLAST hits[1] (% similiar) | Source |
|---|---|---|---|---|
| 19/133 | Bacteroides | acc #DQ907199 | *DQ080146 (95%) | 2,3,4,5-Tetrachlorobiphenyl culture containing Dehalococcoides |
| | | | AY553955 (95%) | PCB contaminanted harbor sediment |
| | | | AY780553 (95%) | Chlorinated ethene-dechlorinating enrichment |
| | | | AJ488070 (90%) | Chlorobenzene degrading consortium |
| | | acc #DQ907201 | *AY217446 (97%) | TCE-dechlorinating community |
| | | | AY217435 (97%) | TCE-dechlorinating community |
| 1/133 | Geobacter | acc #DQ907206 | *AY780563 (98%) | Chlorinated ethene enrichment culture |
| | | | AF223382 (98%) | Isolate that dechlorinates trichloroacetic acid |
| | | | AF447133 (98%) | Population that dechlorinates saturated PCE |
| | | | AF447134 (98%) | |
| | | | AY914177 (98%) | Isolate that dechlorinates PCE |
| | | | AY667270 (97%) | TCE contaminated aquifer |
| 7/133 | Pseudomonas | acc #DQ907203 | AY017341 (99%) | Chlorate-reducing isolate |

*Top BLAST hit.

Figures 8A, 8B:
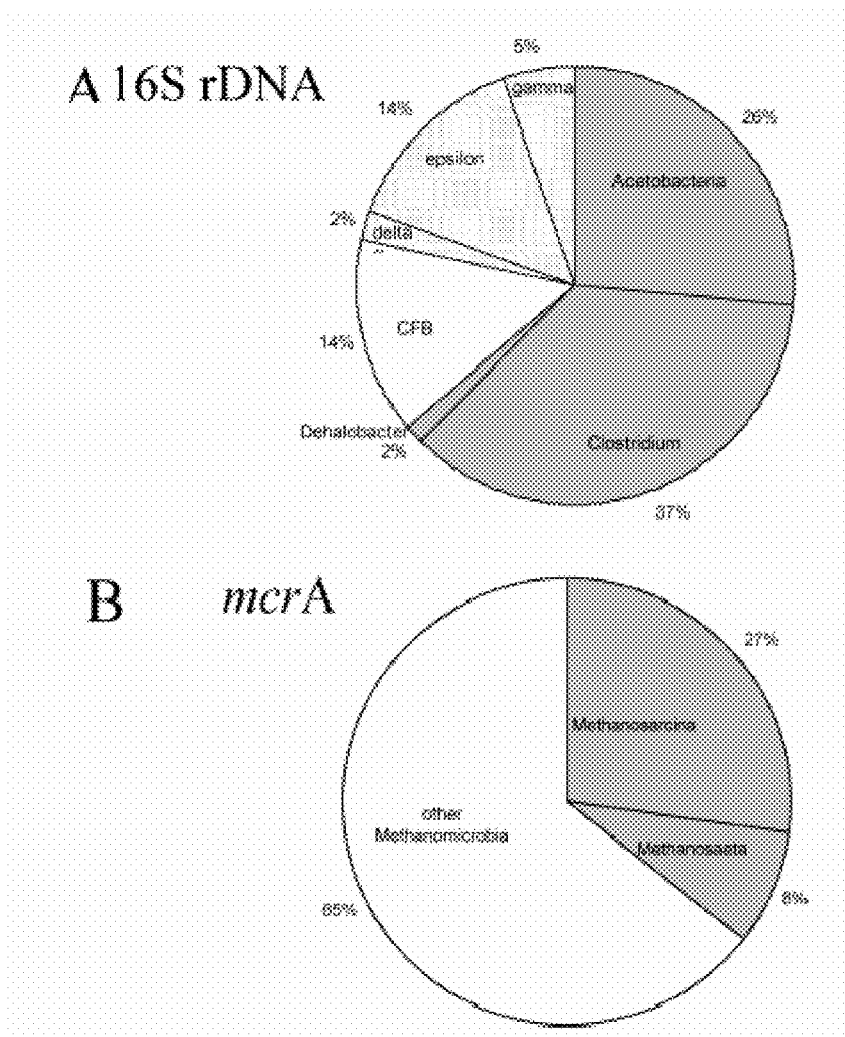
FIGS. 8A-8B illustrate frequency of phylogenetic types in a microbial composition rDNA clone library (A) and mcr clone library (B) according to the present invention.

As shown in FIG. 8A, the 16S rDNA library was dominated by Clostridiales (65%), including three phylotypes. The phylotype representing the greatest number of clones was a Clostridium sp. (SEQ ID NO 1), most closely related (99%) to an uncultured member of a TCE dechlorinating community. The second most prevalent phylotype was an Acetobacterium sp. (SEQ ID NO 2) most closely related (97%) to uncultured clones from a 1,2-dichloropropane-dechlorinating enrichment, and 97% and 96% related to the homoacetogens Acetobacterium malicum and A wieringae, respectively. Less prevalent was a third phylotype, 95% related to an uncultured clone from a TCE-dechlorinating community and 93% related to Dehalobacter restrictus (SEQ ID NO 3), in the evaluated region between 46f and 519r.

There was more variability among sequences of the Bacteroidetes (Cytophaga-flavobacterium-bacteroides group), which accounted for 14% bacterial clones (SEQ ID NO 4 and SEQ ID NO 5). Many of these were related to uncultured clones from dechlorinating populations (Table 2).

Among the Proteobacteria, one clone (delta Proteobacteria) was most closely related (98%) to a Geobacter sp. (SEQ ID NO 6) from a chlorinated ethene enrichment culture, and 98% related to G. lovleyi, a recently described PCE-dechlorinating isolate. The gamma Proteobacteria (SEQ ID NO 7) were 99% related to the top 60 BLAST hits, including Pseudomonas stutzeri and Ps. chloridismutans, that is able to dechlorinate trichloroacetic acid.

For the other phylotypes observed among the bacterial clones (Arcobacter sp. and Desulfobulbus sp., 14% and 2% of the clones, respectively) and all of the mcrA clones, the BLAST database did not reveal relatedness to organisms from dechlorinating populations. Arcobacter sp. comprises part of the epsilon proteobacteria. Desulfobulbus sp., comprises part of the delta proteobacteria.

No Dehalococcoides clones were identified. However, Dehalococcoides numbers determined independently using qPCR and compared with the total number of cells by microscopic count indicated that about 1% of the total consortium population was comprised of Dehalococcoides spp. Microscopic examination confirmed that cocci were rare, and the consortium population was composed almost entirely of rod-shaped cells.

As shown in FIG. 8B, the WBC-2 mcrA clone library was comprised of members of the class Methanomicrobia, and included both acetate- and $H_2$-utilizing methanogens (accession numbers DQ907209 to DQ907221, i.e., SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, and SEQ ID NO 20). Members of the Methanosarcinaceae family are capable of utilizing acetate in the production of methane. These include Methanosarcina spp., which may utilize acetate, $H_2$, methanol, or methyl amines, and Methanosaeta spp., which are obligate acetate utilizers. The other Methanomicrobia are related to methanogens that utilize $H_2$ and formate as electron donors. The presence of Methanosaeta spp. in the WBC-2 culture indicates that acetate is being produced. Although the cultures were methanogenic, methanogens comprised a very small part of the total microbial population of WBC-2. Total methanogens quantified using qPCR comprised 0.2% of the total WBC-2 microbial population.

C. Evidence for a Distinct Dechlorinating Population

The TeCA dechlorination pathway includes reactions that are a part of the more thoroughly studied PCE dechlorination pathway (right half of FIG. 1), and thus might be expected to support the growth of similar organisms. Indeed, the predominance of Clostridia and CFB in the WBC-2 population (Table 2) is also characteristic of TCE-dechlorinating communities, and organisms similar to the ethene-dechlorinating Dehalococcoides and Dehalobacter are observed in WBC-2.

However, the dechlorinating abilities of WBC-2, enriched in the presence of chlorinated ethanes, are different than cultures enriched with chlorinated ethenes, both with respect to the response to added electron donors and in the relative importance of Dehalococcoides within the microbial population. Based on limited studies, the electron donor needs for chlorinated ethane-enriched cultures appear to be different from those of cultures enriched for chlorinated ethene reduction.

Most bacterial isolates capable of reductive dechlorination of chlorinated ethenes, including Dehalococcoides and Dehalobacter, use $H_2$ as the preferred electron donor. The chlorinated ethane-enriched culture, WBC-2, was not stimulated to reduce cisDCE or TCA with $H_2$, $H_2$ plus acetate, or propionate added as the electron donor. The failure of $H_2$ to stimulate dechlorination suggests that the organisms involved are not the same as the chlorinated ethene-reducing organisms that have been studied in isolation. In addition, *Dehalococcoides* spp. comprise only a minor part (about 1%) of the cell population in WBC-2. This, coupled with the presence of consortium members that appear to be closely related to clones of unknown function in other dechlorinating populations, suggests that organisms other than *Dehalococcoides* spp. may play a greater role in TeCA dechlorination. These observations suggest that exposure to chlorinated ethanes results in the selection of a different population of organisms for chlorinated ethene reduction. Cultures that were enriched using chlorinated ethenes (i.e., in the absence of chlorinated ethanes) were inhibited in the presence of chlorinated ethanes.

D. Microbial Roles within WBC-2

The specific roles of WBC-2 consortium members have yet to be determined. Although tentative roles could be assigned to *Dehalococcoides* (cisDCE, transDCE, VC, and DCA reduction), *Dehalobacter* (TCA reduction to VC, DCA reduction to ethene), and *Acetobacterium* (DCA reduction to ethene) based on studies of related organisms, WBC-2 exhibited some capabilities, such as TeCA reduction to transDCE, and TCA reduction to DCA, for which no organisms have been implicated.

The observation of closely related phylotypes in WBC-2 and other dechlorinating communities, such as *Clostridium* sp., *Acetobacterium* sp., and CFB provides some evidence for the involvement of previously unrecognized bacteria in dechlorination processes. However, enrichment of organisms in a dechlorinating system provides only circumstantial evidence for direct involvement. In WBC-2, lactate fermentation, homoacetogenesis, methanogenesis, sulfur cycling, syntrophy, and chemoautotrophy could support organisms in the culture without deriving energy from dechlorination. The possible role of methanogens in dechlorination by WBC-2 is not known. Although the presence and activity of methanogens are often considered to be inhibitory to or at least contraindicative of dechlorination activity, some evidence suggests that methanogens may play an important role in dechlorination.

Example

Bioremediation with WBC-2

WBC-2 was able to degrade chlorinated ethanes and ethenes simultaneously with little VC accumulation. This capability makes the microbial consortium WBC-2 a potentially valuable tool for bioremediation of sites contaminated with mixtures of chlorinated ethenes and ethanes. In addition, the simultaneous reduction of all components of the TeCA degradation pathway can reduce the total treatment time and help prevent transport of hazardous compounds out of the treatment zone.

An innovative, enhanced bioremediation pilot test was designed and installed in a seep at the ground-water/surface-water interface within the tidal wetland along West Branch Canal Creek at Aberdeen Proving Ground, Maryland, to treat a mixture of dissolved chlorinated methanes, ethenes, and ethanes.

First-order degradation rates were estimated by circulating increasing concentrations of site contaminant mixtures through continuous, up-flow columns comprised of a commercially available compost, peat, and sand-matrix (with and without zero-valent iron).

Columns were bioaugmented with a mixed anaerobic consortium (WBC-2). The tolerable thickness of the bioreactive mat at this site was determined based on sediment strength, bearing capacity, and estimated settlement over time. Thus, the bioreactive mat was comprised of two reactive zones: (1) a lower zone (nearest the sediment) designed to enhance abiotic degradation of chlorinated methanes, and (2) an upper zone designed to enhance biodegradation of the remaining chlorinated methanes, ethanes, and ethenes. The lower zone was comprised of zero-valent iron filings and an organic matrix consisting of commercially-available compost, peat, and sand. The upper zone was comprised of a compost, peat, and sand matrix and was bioaugmented with WBC-2.

Example

Methods and Materials

I. Development of WBC-2 Anaerobic Microbial Composition

Sediment was collected from two sites within the wetland at West Branch Canal Creek (WB23 and WB30) and prepared anaerobically. Sediments were collected, sieved, slurried with groundwater (1:1.5), and incubated (19° C.) with TeCA (7 µM) in 1-L serum bottles without headspace for 1 month. Most of the Fe(III) and sulfate (alternative electron acceptors) were depleted during this incubation period and methane was being produced. Aliquots (100 ml) of sediment slurries were then transferred to 120-ml serum bottles with a $N_2/CO_2$ (95:5) headspace and amended with a daughter compound, cisDCE or TCA, for 1 to 2 months. In all sediment slurry enrichments, the electron donors were derived only from organic matter in the sediment.

Sediment slurries (100 ml each of TCA-enriched WB23 and cisDCE-enriched WB30) were then transferred into an anaerobic culture medium as described below (1800 ml) with sulfide (50 µM) added as a reductant, and amended with target concentrations of TeCA (30 µM) or a mixture of TeCA (25 µM), TCA (50 µM), and cisDCE (50 µM). The electron donor for cultivation was selected in tests on the TeCA amended culture (see below) 3 weeks after inoculation from sediment slurry. Cultures were diluted over a 2-year period and contain about 0.1% sediment by volume.

II. Evaluation of Electron Donors

All electron donor tests were performed in duplicate on sub samples removed from TeCA-depleted stock culture. Because concentrations of intermediates often are low or undetectable during TeCA degradation by WBC-2, TCA and cisDCE were used as test compounds to ensure that the electron donor selected would support both chlorinated ethane and chlorinated ethene pathways. In addition, the ability of each electron donor to support the dechlorination of VC was evaluated.

Aliquots of WBC-2 culture (10 ml) were transferred anaerobically to 28-ml pressure tubes filled with $N_2/CO_2$ (80:20). WBC-2 was evaluated for dechlorination of test compounds in the following electron donor treatments: propionate (10 mM); succinate (3 mM); lactate (3 mM); pyruvate (3 mM); benzoate (3 mM); formate (10 mM); acetate (10 mM); $H_2$ (20 kPa overpressure, added three times during the incubation) with or without acetate (1 mM) added as a carbon source; whey (5 g/L); no electron donor added.

The electron donors supplied electron equivalents (assuming complete oxidation) equal to about 100 times that required for the reduction of the chlorinated compounds, cisDCE or TCA, which were added from aqueous emulsions (for a final concentration of approximately 1 and 0.75 mM, respectively) and monitored for VC and DCA production. The ability to dechlorinate VC was tested by adding VC (4.2 µM) from a gaseous standard (Matheson, Twinsburg, Ohio) in a separate treatment. All treatments were incubated at 19° C. and monitored by sampling the headspace for analysis with a gas chromatograph (GC) with a flame ionization detector (FID).

As shown in Table 1 below, the electron donor for WBC-2 cultivation was selected by comparing dechlorination in electron donor treatments with dechlorination in a control with no added electron donor. Controls with no added electron donor exhibited decreases in added TCA and cisDCE characteristic of adsorption, with an initial decrease of 24% and 10%, respectively, followed by no further decrease. Less than 1% of the added TCA or cisDCE in the controls was reduced to VC and no DCA was produced. $H_2$ did not stimulate reduction of TCA or cisDCE above that observed in the controls, whether or not acetate was added as a carbon source.

The most complete dechlorination was obtained in treatments with lactate and pyruvate. The pathway of TCA reduction (production of VC versus DCA from TCA) varied among electron donor treatments. Cultures with lactate produced more DCA relative to VC than did cultures with pyruvate. No DCA was produced in treatments with propionate, acetate, benzoate, or whey.

TABLE 1

WBC-2 Reduction of cDCE, TCA, and VC

| Electron donor | Degradation relative to no electron donor | | |
|---|---|---|---|
| | cDCE | TCA | VC |
| Succinate | + | +/− | − |
| Lactate | ++ | +++ | +++ |
| Pyruvate | + | ++ | +++ |
| Benzoate | − | + | ND |
| Propionate | + | − | − |
| Formate | − | − | + |
| Acetate | − | − | − |
| $H_2$ | − | − | +++ |
| $H_2$, with 1 mM acetate | − | − | +++ |
| Whey | − | − | ND |

+++, complete dechlorination (TCA [0.75 mM], DCE [1 mM] after 27 days, or VC [4.2 µM] after 3 days).
++, dechlorination at least 50% complete.
+, greater than no electron donor control.
+/−, one duplicate greater than control.
−, dechlorination not greater than no electron donor control.
ND, treatment not done.

III. Culture Medium and Maintenance

The anaerobic medium included (g/L deionized water): $NaHCO_3$ (2.5), $NH_4Cl$ (0.5), $NaPO4$ (0.5), KCl 0.1), 10 ml vitamin solution, and 10 ml trace mineral solution, with a gas phase of $N_2$ and $CO_2$ (80:20). The trace mineral solution contained (g/L): Nitrilotriacetic acid (1.5), $MgSO_4.7H_2O$ (3.0), $MnSO_4.H_2O$ (0.5), NaCl (1.0), $FeSO_4.7H_2O$ (0.1), $CaCl_2.2H_2O$ (0.1), $CoCl_2.6H_2O$ (0.1), $ZnCl_2$ (0.13), $CuSO_4.5H_2O$ (0.01), $AlK(SO_4)_2.12H_2O$ (0.01), $H_3BO_3$ (0.01), $Na_2MoO_4$ (0.025), $NiCl_2.6H_2O$ (0.024), $Na_2WO_4.2H_2O$ (0.025).

Early in development, some batches were starved for periods as long as several months, but recovered activity when feeding was resumed. Once established, cultures were maintained either with lactate (1 mM) and TeCA (50 µM) added from aqueous stocks once or twice weekly, or lactate (1.5 mM) and TeCA (25 µM), TCA (50 µM), and cisDCE (50 µM). The ratio of electron equivalents for donors to acceptors was 30 and 17, respectively, for stocks maintained with TeCA and the chlorinated mixture. The chlorinated stocks were prepared by adding purified standards to sterile anaerobic deionized water. Chlorinated stock bottles were vigorously shaken prior to each amendment in order to emulsify any undissolved compound. The cisDCE contained approximately 1% trans-DCE.

WBC-2 was maintained in 2 L batches of medium from which culture volumes were removed for study. After 1 year, all cultures were restored to full 2 L volume by adding fresh medium. Under contract by the U.S. Army, samples of WBC-2 were given to SiREM Laboratories (Guelph, Ontario, Canada) for propagation of the culture to the large volumes required for field bioremediation tests conducted by the U.S. Geological Survey, using lactate and the chlorinated mixture described above (GeoSyntec Consultants Inc., 2004). WBC-2 microbial composition (clone analysis) was assessed in a culture sample obtained from SiREM Laboratories that had been scaled up by transferring two times into fresh medium.

IV. Gas Analysis

Culture headspace was sampled using a gas tight syringe and injected into one or both of the following GC-FID systems. For rapid analysis of TeCA, TCA, DCA, TCE, cisDCE, transDCE, and VC, a Hewlett-Packard model 5890 series II with isothermal separation at 100° C. on a VOCOL (Supelco, Bellefonte, Pa.) capillary column (30 m×0.53 mm) was used. For separation of methane, ethene, and ethane, and for analysis of VC, transDCE, and cisDCE when interfering peaks were present, a Shimadzu model GC-17A with separation on a Rt Q-Plot (Restek, Bellefonte, Pa.) column (30 m×0.32 mm) using a temperature program of 100° C. for 5 min, ramping to 200° C. at 20° C./min was used.

Aqueous standards of chlorinated compounds were prepared from highly purified neat calibration standards. Standards of chlorinated compounds were prepared by adding 10 µl of neat solution to 100 ml water, and preparing aqueous dilutions for headspace analysis in bottles sealed with Teflon coated stoppers. Dimensionless Henry's law constants (DHLCs), were used to calculate expected headspace concentrations from known liquid concentrations. Methane, ethene, and ethane standards were purchased as gas standards (Scott Specialty Gas). Concentrations of chlorinated compounds and non-chlorinated end products in samples of WBC-2 culture headspace were converted to dissolved values using DHLCs and total concentrations (per volume medium) were calculated. DHLCs have been measured empirically by many researchers and vary widely. The chosen DHLCs fall in the midrange of published values. Nonetheless, the DHLCs are the greatest source of possible error in the concentrations reported here, and may exceed 10%. Errors between repeat injections are about 2%.

The dimensionless Henry's law constants (DHLC) applied were 0.019 for TeCA, 0.556 for TCA, 0.1821 for DCA, 0.3056 for TCE, 0.1255 for cisDCE, 0.3056 for transDCE, 0.9087 for VC, 7.96 for ethene, 19.88 for ethane, and 28.5 for methane. All detection limits were less than 0.01 µM.

V. Monitoring WBC-2 Dechlorination

A simple method was used for monitoring dechlorination, based on partitioning in the headspace. However, the stoichiometry of TeCA to its degradation products is difficult to determine using this method. Both adding and measuring the initial concentration of TeCA involved potentially large errors. Dilution of the stock solution cannot be relied upon to determine the amount of TeCA added, because TeCA in the stock solution was not completely dissolved and possibly not completely homogenized by shaking. TeCA measurements were subject to two known sources of error. First, when calculating total concentrations from headspace values, errors are magnified for compounds with a very low DHLC. The DHLC for TeCA (0.019) was an order of magnitude lower than any other compound measured and therefore subject to the greatest error. Conversely, compounds such as methane, ethene and ethane are largely partitioned to the headspace and subject to the least error. Second, because there is some sediment as well as cell mass in the cultures, distribution of TeCA between the liquid and gas phases may be complicated by adsorption, resulting in a discontinuity between TeCA uptake and the appearance of end poduct. All of these errors may have contributed to differences between target TeCA additions and measured concentrations (e.g., target addition of 60 µM versus measured concentration, 240 µM, that is reported in FIG. 2), as well as the error in stoichiometry between different bottles (i.e., 2±1).

VI. Cloning, RFLP Screening and Sequencing, TRFLP

DNA was extracted using the Bio-101 Fast DNA Spin Kit for Soil (MP Biomedicals, Irvine, Calif.) following manufacturers instructions, except that product recovery was maximized at each step. Bacterial and methanogen DNA were amplified using the polymerase chain reaction (PCR) in a Perkin Elmer Geneamp 2400 thermal cycler with 16S rDNA (46f and 519r) primers and methyl coenzyme-M reductase (mcrAf and mcrAr) primers, respectively. 16S rDNA PCR conditions (30 cycles) were denaturing at 94° C. (30 s), annealing at 56° C. (30 s), and extension at 72° C. (1 min).

Microbial members of the consortium were characterized by cloning and sequencing the bacterial 16S rDNA and mcrA amplicons. Amplicons were purified using the Wizard PCR purification kit (Promega, Madison, Wis.) and cloned using the TA cloning kit or the Topo TA cloning kit for sequencing according to manufacturer's instructions (Invitrogen, San Diego, Calif.). Colonies were picked and 16S rRNA and mcrA gene clone fragments (133 and 48, respectively) were recovered using vector primers and mcrA primers, respectively, using PCR. For the bacterial 16S rDNA characterization, the PCR products were reamplified using 46f and 519r primers. All PCR amplicons were digested with restriction enzymes (6 µl of PCR product with 2.5 U each of MspI and HinPI) according to manufacturer's instructions (Promega, Madison, Wis.). Restriction fragments were analyzed by size separation on a 3.5% Metaphor (Cambrex, Rockland, Me.) agarose gel, restriction fragment length polymorphism (RFLP) patterns were distinguished, and the frequency with which each pattern occurred was determined.

It should be noted that the frequency of clones in the library may not correspond directly to relative phylotype numbers in the culture due to undefined differences in the number of 16S rDNA copies per cell. In addition, PCR and nucleic extraction biases may contribute to apparent differences in the abundance of RFLP patterns. Representative clones for each pattern were selected for sequencing. Amplicons to be sequenced were purified with the wizard PCR purification system, and cycle sequencing was performed on both strands using Big Dye v3.1 (Applied Biosystems, Foster City, Calif.) and run on an ABI310 genetic analyzer. Sequences were edited and assembled using Autoassembler (Applied Biosystems, Foster City, Calif.). Closest phylogenetic relatives were determined by BLAST search of the National Center of Bioinformatics (NCBI) database (http://www.ncbi.nlm.nih.gov/).

Terminal restriction fragment length polymorphism (TRFLP)—PCR was performed as described above, but using 46f primer with FAM label attached. A restriction digest of 6 µl of PCR product was performed using 5U MnII (New England Biolabs, Beverly, Mass.). Digested samples were precipitated with 0.1 volume of 3 M sodium acetate and 2 volumes of cold 100% ethanol and resuspended in 10 µl sterile water. A 2.5 µl aliquot of the digested sample was added to 12 µl of deionized formamide and 0.5 µl ROX500 standard (Applied Biosystems). Samples were denatured at 95° C. for 5 min. DNA fragments were separated using an ABI310 sequencer (Applied Biosystem). Terminal restriction fragments were detected using 310Genescan analytical software, version 2.1.1, resulting in a TRFLP profile for each sample.

VII. Detection and Quantification of Specific Members by Quantitative PCR

Primers were used to detect organisms with abundances too low to be detected in the 16S clone library, including two known dechlorinators, *Dehalococcoides* spp., and *Desulfuromonas* spp., and methanogens. DNA copy number in an extract of WBC-2 DNA was determined by quantitative PCR (qPCR) using the quantitect SYBR green real-time PCR kit (Qiagen, Chatsworth, Calif.) and the Opticon real-time PCR system (MJ Research, now BioRad, Hercules, Calif.).

The 16S rDNA based primers used to target *Dehalococcoides* were dhc730f, 5'-GCG GTT TTC TAG GTT GTC-3' (SEQ ID NO 21) and dhc1350r, 5'-CAC CTT GCT GAT ATG CGG-3' (SEQ ID NO 22). The *Desulfuromonas* primers (designed for specificity to *Desulfuromonas* sp. strain BB1 and *D. chloroethenica* 16S rDNA) and conditions are known (Löffler et al., 2000). Methanogens were quantified using mcrA primers (Luton et al., 2002). A standard curve was determined using Ct values of serial dilutions of plasmid containing the dhc or mcrA amplified fragment, or the *Desulfuromonas* sp. strain BB1 amplicon of known concentration (and thus copy number), and the samples were plotted against that curve to determine abundance. Calculations of cell numbers were based on one 16S rDNA copy per cell for *Dehalococcoides* (www.tigr.org), and 1 mcrA copy per cell for methanogens. For the purposes of calculating cell numbers, nucleic acid extractions were assumed to be perfect, because no measurement of extraction efficiency is available. For microscopic counts, culture samples were suspended in 0.01% Triton X-100 and stained with 5 µg/ml 4',6-diamidino-2-phenylindole (DAPI) in 1× phosphate-buffered saline (PBS), filtered onto a black Nuclepore filter (0.2 µM), and viewed using epi-fluorescence.

Although the present invention has been described in terms of particular exemplary and alternative embodiments, it is not limited to those embodiments. Alternative embodiments, examples, and modifications which would still be encompassed by the invention may be made by those skilled in the art, particularly in light of the foregoing teachings.

What is claimed is:

1. A microbial composition for concurrent dechlorination of a mixture of chlorinated ethanes and chlorinated ethenes, comprising an isolated bioremediative consortium comprising strains of microorganism comprising *Clostridium, Acetobacter, Dehalobacter, Bacteroides*, Proteobacteria, and *Dehalococcoides*,
wherein the bioremediative consortium is obtained by culturing microbes of a sediment sample obtained from a site contaminated with a mixture of chlorinated ethanes and chlorinated ethenes in an anaerobic medium with at least one chlorinated ethane and an electron donor selected from the group consisting of lactate, succinate, pyruvate, benzoate, propionate, and formate.

2. A microbial composition according to claim 1, wherein the consortium further comprises Methanomicrobia.

3. A microbial composition according to claim 2, wherein the consortium comprises at least one of *Methanosarcina* or *Methanosaeta*.

4. A microbial composition for concurrent dechlorination of a mixture of chlorinated ethanes and chlorinated ethenes, comprising:
a non-naturally occurring consortium of dechlorinatingly effective microbial species, wherein said consortium of dechlorinatingly effective microbial species comprises
a 16S rDNA nucleic acid sequence that has more than 99% identity to a nucleic acid sequence consisting of SEQ ID NO 1,
a 16S rDNA nucleic acid sequence that has more than 97% identity to a nucleic acid sequence consisting of SEQ ID NO 2, and
a 16S rDNA nucleic acid sequence that has more than 95% identity to a nucleic acid sequence consisting of SEQ ID NO 3.

5. A microbial composition according to claim 4, wherein the consortium further comprises at least one 16S rDNA a nucleic acid sequence that has more than 97% identity to a nucleic acid sequence consisting of SEQ ID NO 4 or SEQ ID NO 5.

6. A microbial composition according to claim 4, wherein the consortium further comprises at least one 16S rDNA a nucleic acid sequence that has more than 98% identity to a nucleic acid sequence consisting of SEQ ID NO 6.

7. A microbial composition according to claim 4, wherein the consortium further comprises at least one methyl coenzyme-M reductase nucleic acid sequence consisting of SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, or SEQ ID NO 20.

8. A method for dechlorinating chlorinated waste, comprising:
- contacting at least one of chlorinated ethanes, chlorinate ethenes or chlorinated methanes with a microbial composition according to claim 4; and
- anaerobically dechlorinating at least one of the chlorinated ethanes, chlorinate ethenes, or chlorinated methanes.

9. A method according to claim 8, wherein the chlorinated waste comprises contaminated soil or contaminated water.

10. A microbial composition according to claim 4, wherein said consortium of dechlorinatingly effective microbial species comprises:
- a 16S rDNA nucleic acid sequence consisting of SEQ ID NO 1,
- a 16S rDNA nucleic acid sequence consisting of SEQ ID NO 2, and
- a 16S rDNA nucleic acid sequence consisting of SEQ ID NO 3.

11. A microbial composition according to claim 4, wherein the consortium further comprises at least one 16S rDNA a nucleic acid sequence that has more than 99% identity to a nucleic acid sequence consisting of SEQ ID NO 7.

12. A microbial composition for concurrent dechlorination of a mixture of chlorinated ethanes and chlorinated ethenes, comprising an isolated bioremediative consortium comprising:
- *Clostridium* having a 16S rDNA nucleic acid sequence consisting of SEQ ID NO 1;
- *Acetobacter* having a 16S rDNA nucleic acid sequence consisting of SEQ ID NO 2; and
- *Dehalobacter* having a 16S rDNA nucleic acid sequence consisting of SEQ ID NO 3.

13. A microbial composition according to claim 12, further comprising:
- *Bacteroides* having a 16S rDNA nucleic acid sequence consisting of SEQ ID NO 4 or SEQ ID NO 5;
- Proteobacteria having a 16S rDNA nucleic acid sequence consisting of SEQ ID NO 6 or SEQ ID NO 7; and
- *Dehalococcoides*.

* * * * *

SEQUENCE LISTING

<160> NUMBER OF SEQ ID NOS: 22

<210> SEQ ID NO 1
<211> LENGTH: 425

```
<212> TYPE: DNA
<213> ORGANISM: Unknown
<220> FEATURE:
<223> OTHER INFORMATION: uncultured bacterium

<400> SEQUENCE: 1
gcgagatgat ctcttcgggg agattctagc ggcggacggg tgagtaacac gtgggtaacc    60
tgcctcaaag aggggatag cctcccgaaa gggagattaa taccgcataa cattattttc    120
tcgcatgaga agataatcaa aggagcaatc cgctttgaga tggacccgcg gcgcattagc   180
tagttggtga ggtaacggct caccaaggcg acgatgcgta gccgacctga gagggtgatc   240
ggccacattg gaactgagac acggtccaga ctcctacggg aggcagcagt ggggaatatt   300
gcgcaatggg ggaaccctg acgcaagcaa cgccgcgtga gtgatgaagg tcttcggatt   360
gtaaagctct gtctttgggg acgataatga cggtacccaa ggaggaagcc acggctaact  420
acgtg                                                              425

<210> SEQ ID NO 2
<211> LENGTH: 430
<212> TYPE: DNA
<213> ORGANISM: Unknown
<220> FEATURE:
<223> OTHER INFORMATION: uncultured bacterium

<400> SEQUENCE: 2
agtcgagcga gatgatccct ccgggagatt ctagcggcgg acgggtgagt aacgcgtggg    60
taacctgccc tatggaaagg aatagcctcg ggaaactggg agtaatgcct tataatacat   120
tttggtcgca cgactatgat gttaaacgct ccggtgccat aggatggacc cgcgtcccat   180
tagctagttg gtgagataac agcccaccaa ggcgacgatg gtaaccggg tctgagaggg    240 cgaacggtca cactggaact gagacacggt ccagactcct acgggaggca gcagtgggga   300
atattgcgca atgggggcaa ccctgacgca gcaataccgc gtgagtgaag aaggttttcg    360
gatcgtaaag ctctgttatt gggaagaaa aaagacggta cccaagaaga aagtcccggc    420
taactacgtg                                                         430

<210> SEQ ID NO 3
<211> LENGTH: 478
<212> TYPE: DNA
<213> ORGANISM: Unknown
<220> FEATURE:
<223> OTHER INFORMATION: uncultured bacterium

<400> SEQUENCE: 3
agtcgaacgg agtaataaaa taagtttact tagattatta cttagtggcg aacgggtgag    60
taacgcgtgg gtaacctgcc cttaagaccg ggacaacagc tggaaacggc tgctaatacc   120
ggatggattt attggaaggc atcttctaat aaggaaagct ggcctctgta tatgctagcg   180
cttagggatg gatccgcgtc tgattagcta gttggtaggg taatggccta ccaaggcgac   240
gatcagtagc cggcctgaga gggtaaacgg ccacactggg actgagacac ggcccagact   300
cctacgggag gcagcagtgg ggaatcttcc gcaatgggacg aaagtctgac ggagcaacgc   360
cgcgtgtatg aagaaggcct tcgggttgta aaatactgtt gttggggaag aacggctgga   420
gtgtaaataa tgcttcagat tgacggtacc caacgaggaa gccccggcta actacgtg      478

<210> SEQ ID NO 4
<211> LENGTH: 447
<212> TYPE: DNA
<213> ORGANISM: Unknown
```

<220> FEATURE:
<223> OTHER INFORMATION: uncultured bacterium

<400> SEQUENCE: 4

```
ggggcagcac aaggagcaat ctgaggtggc gaccggcgca cgggtgagta acacgtatgc    60
aacctgtctg taagcgggga ataacccgtt gaaagacgga ctaataccgc ataatactgg   120
agatctgcat ggatattcag ttaaacattt atggcttaca gatgggcatg cgcatgatta   180
gatagttgga gaggtaacgg ctccccaagt caacgatcat taggggttct gagaggaagg   240
tcccccacac tggtactgag acacggacca gactcctacg ggaggcagca gtgaggagta   300
ttggtcaatg ggcgagagcc tgaaccagcc aagtcgcgtg caggaagaat gtcctatgga   360
ttgtaaactg cttttgcagg ggaataaagt gagccaccgt gtggtttttt gtatgtactc   420
tgcgaataag gatcggctaa ctccgtg                                       447
```

<210> SEQ ID NO 5
<211> LENGTH: 454
<212> TYPE: DNA
<213> ORGANISM: Unknown
<220> FEATURE:
<223> OTHER INFORMATION: uncultured bacterium

<400> SEQUENCE: 5

```
ggggcagcac gggagtagca atacaactgg tggcgaccgg cgcacgcgtg agtaacgcgt    60
atgcaaccta cctatcagag gggaataacc cggcgaaagt cggactaata ccgcataaaa   120 caggggggcac cgcatggtga tatttgttaa agaattcgct gatagatggg catgcgttcc   180
attagggtag ttggtgaggt aacggctcac caagccgacg atggataggg gaactgagag   240
gttggtcccc cacactggta ctgagacacg gaccagactc ctacgggagg cagcagtgag   300
gaatattggt caatgggcga gagcctgaac cagcccaagt cgcgtgaagg aagaaggatc   360
tatggtttcg taaacttctt tttgcagggg aataaagtgc gggacgtgtc ctgtttcgta   420
tgtaccctga gaataaggat cggctaactc cgtg                               454
```

<210> SEQ ID NO 6
<211> LENGTH: 464
<212> TYPE: DNA
<213> ORGANISM: Unknown
<220> FEATURE:
<223> OTHER INFORMATION: uncultured bacterium

<400> SEQUENCE: 6

```
acggagtgaa ggagcttgct ctttcattta gtggcgcacg ggtgagtaac gcgtagataa    60
tctgccttag actctgggat aacatctcga aagggggtgct aataccggat aagcccacga   120
tggcgtaagt cattgcggga aaaggggggcc tctgaatatg ctcttgatct aagatgagtc   180
tgcgtaccat tagctagttg gtagggtaag agcctaccaa ggcgacgatg gttagctggt   240
ctgagaggat gatcagccac actggaactg agacacggtc cagactccta cgggaggcag   300
cagtggggaa ttttgcgcaa tgggggaaac cctgacgcag caacgccgcg tgagtgatga   360
aggctttcgg gtcgtaaagc tctgtctaga gggaagaaat gataatcggt taatacccgg   420
ttttcttgac ggtacctctg aaggaagcac cggctaactc cgtg                    464
```

<210> SEQ ID NO 7
<211> LENGTH: 446
<212> TYPE: DNA
<213> ORGANISM: Unknown
<220> FEATURE:
<223> OTHER INFORMATION: uncultured bacterium

<400> SEQUENCE: 7

```
gcggatgaag ggagcttgct ctctgattca gcggcggacg ggtgagtaat gcctaggaat      60
ctgcctgata gtgggggaca acgtttcgaa aggaacgcta ataccgcata cgtcctacgg     120
gagaaagcag gggaccttcg ggccttgcgc tatcagatga gcctaggtcg gattagctag    180
ttggtgaggt aacggctcac caaggcgacg atccgtaact ggtctgagag gatgatcagt    240
cacactggaa ctgagacacg gtccagactc ctacgggagg cagcagtggg gaatattgga    300
caatgggcga aagcctgatc cagccatgcc gcgtgtgtga agaaggtctt cggattgtaa    360
agcactttaa gttgggagga agggcattaa cctaatacgt tagtgttttg acgttaccga    420
cagaataagc accggctaac ttcgtg                                           446
```

<210> SEQ ID NO 8
<211> LENGTH: 433
<212> TYPE: DNA
<213> ORGANISM: Unknown
<220> FEATURE:
<223> OTHER INFORMATION: uncultured archaeon

<400> SEQUENCE: 8

```
tgcatacacc gatgacatcc tcgacaacaa cgtgtactac gacgttgact acatcaacga     60
caagtacaac ggtgcagcaa ccatcggcaa ggacaacaag atcaaggcca ccctcgacgt    120
cgtaaaggac atcgcaaccg agtccactat ctacggtatc gagacctacg agaagttccc    180
gactgccctt gaagaccact tcggtggatc ccagagagca accgtgctcg cagctgcagc    240
cggtgtcgca acctccctcg caaccgcaaa tgcaaatgct ggtctctccg gctggtacct    300
ctccatgtac ctgcacaagg aagcatgggg ccgtctcggc ttcttcggat acgacctgca    360
ggaccagtgc ggtgccacaa acgttctgtc ctaccagggc gacgaaggtc tcccagacga    420
actccgtggt cca                                                         433
```

<210> SEQ ID NO 9
<211> LENGTH: 415
<212> TYPE: DNA
<213> ORGANISM: Unknown
<220> FEATURE:
<223> OTHER INFORMATION: uncultured archaeon

<400> SEQUENCE: 9

```
agcatacacc gacaacattc tcgacgagtt cacctactac ggtatggact acttaaagga     60
caagtacggc ggctactcgc aggcaccagc aacccaggag gtcgtcaacg acctcgcaac    120
tgaggtcacg ctgaacgcca tggagcagta cgagcagttc ccaaccatga tggaggacca    180
cttcggcggt tcccagcgtg ctggtgtcat tgcagcagca tcaggtttga ccactgcaat    240
cggtaccggg aactccaatg ccggtctgaa cggctggtac ctctcgatgc tcatgcacaa    300
ggaaggatgg tcacgtctcg gtttcttcgg ctacgacctg caggaccagt gtggttcagc    360
aaactcgatg tcgatcagac cggatgaagg tctcctcggt gaactccgtg gacca         415
```

<210> SEQ ID NO 10
<211> LENGTH: 432
<212> TYPE: DNA
<213> ORGANISM: Unknown
<220> FEATURE:
<223> OTHER INFORMATION: uncultured archaeon

<400> SEQUENCE: 10

```
tgcatacacc gatgacatcc tcgacaacaa cgtgtactac gacgttgact acatcaacga     60
```

```
caagtacaac ggtgctgcaa ccatcggcaa ggacaacaaa gtaaaggcaa ccctcgacgt      120
cgtaaaggac atcgcaaccg agtccactat ctacggtatc gagacctacg agaagttccc      180
gactgccctt gaagaccact tcggtggatc cagagagca accgtgctcg cagctgcagc       240
cggtgtcgca acctccctcg caaccgcaaa cgccaacgct ggtctctccg gctggtacct      300
ctccatgtac ctgcacaagg aagcatgggg cgtctcggct tcttcggata cgacctgcag      360
gaccagtgcg gtgccacaaa cgttctgtcc taccagggcg acgaaggtct cccagacgaa      420
ctccgtggtc ca                                                          432

<210> SEQ ID NO 11
<211> LENGTH: 432
<212> TYPE: DNA
<213> ORGANISM: Unknown
<220> FEATURE:
<223> OTHER INFORMATION: uncultured archaeon

<400> SEQUENCE: 11
tgcatacacc gatgacatcc tcgacaacaa cgtgtactac gacgttgact acatcaacga      60
caagtacaac ggtgctgcaa ccaccggcaa ggacaacaaa gtaaaggcaa ccctcgacgt      120
cgtaaaggac atcgcaaccg agtccactat ctacggtatc gagacctacg agaagttccc      180
gactgccctt gaagaccact tcggtggatc cagagagca accgtgctcg cagctgcagc       240
cggtgtcgca acctccctcg caaccgcaaa cgccaacgct ggtctctccg gctggtacct      300
ctccatgtac ctgcacaagg aagcatgggg cgtctcggct tcttcggata cgacctgcag      360
gaccagtgcg gtgccacaaa cgttctgtcc taccagggcg acgaaggtct cccagacgga      420
ctccgtggtc ca                                                          432

<210> SEQ ID NO 12
<211> LENGTH: 433
<212> TYPE: DNA
<213> ORGANISM: Unknown
<220> FEATURE:
<223> OTHER INFORMATION: uncultured archaeon

<400> SEQUENCE: 12
tgcatacact gatgacatcc tcgacaacaa cgtgtactac gacgttgact acatcaacga      60
caagtacaac ggtgctgcaa cagtcggcaa ggacaacaag gtaaaggcaa ccctcgaagt      120
cgtaaaggac atcgcaaccg agtccacact ctacggtatc gagacctacg agaaattccc      180
aaccgccctt gaagaccact tcggtggatc cagagagca accgtgctcg cagctgcagc       240
cggtgtcgca tgtgcactcg gaactgcaaa cgccaatgct ggtctctcag gctggtacct      300
ctccatgtac ctgcacaagg aagcatgggg cagactcggc ttcttcggat acgacctgca      360
ggaccagtgc ggtgccacaa cgttctgtc ctaccagggc gacgaaggtc tcccagacga      420
actccgtggt cca                                                         433

<210> SEQ ID NO 13
<211> LENGTH: 415
<212> TYPE: DNA
<213> ORGANISM: Unknown
<220> FEATURE:
<223> OTHER INFORMATION: uncultured archaeon

<400> SEQUENCE: 13
tgcatacacc gacaacatcc tcgatgacta caccgagtac ggtattgact acgtcaagaa      60
gaaacacggt ggcatcggca aggcaaagtc aacccaggaa gttgtcagcg acattgcaac      120
```

```
cgaggtcaac ctctacggta tggagcagta cgaacagtac ccgaccgccc tcgagagcca      180
cttcggtgga tcccagcgtg cgtctgtcct tgcagcagca tcaggtattt cctgttcaat      240
ggcaacggca aactccaacg ctggcctgaa cggctggtac ttgtccatgc tcatgcacaa      300
ggaaggctgg tcacgtcttg gcttcttcgg ctacgacctg caggaccagt gcggttccgc      360
aaactccatg tcgatccgtc ccgacgaggg attactcggc gagctccgtg daccg          415
```

<210> SEQ ID NO 14
<211> LENGTH: 437
<212> TYPE: DNA
<213> ORGANISM: Unknown
<220> FEATURE:
<223> OTHER INFORMATION: uncultured archaeon

<400> SEQUENCE: 14

```
tgcatacacc gacaacatcc tcgatgacta cacctactac ggtatggatt acatcaagga      60
caagtacaaa gtcaactgga agagcccgtc agccaaggac aaggtcaagc caacccagga     120
tctcgtcaat gagctcgcta ccgaagttac actctacggt atggagcagt acgagcagtt     180
cccgacccct atggaagacc acttcggtgg atcccagcgt gctggtgttc tcgcagctgc     240
atccggtctt acctgtgcaa tcgccaccgg taactccaac gctggcctga acggctggta     300
cctgtccatg cttgcccaca aggaaggctg gtcacgtctc ggcttcttcg gctacgacct     360
tcaggaccag tgcggttccg caaactcgct ctctatcaga cctgacgaag gctgtatcgg     420
cgagctccgt ggacccg                                                    437
```

<210> SEQ ID NO 15
<211> LENGTH: 415
<212> TYPE: DNA
<213> ORGANISM: Unknown
<220> FEATURE:
<223> OTHER INFORMATION: uncultured archaeon

<400> SEQUENCE: 15

```
agcatacacc gacaacattc tcgacgagtt cacctactac ggtatggact acttaaagga      60
caagtacggc ggctactcgc aggcaccagc aacccaggag gtcgtcaacg acctcgcaac     120
tgaggtcacg ctgaacgcca tggagcagta cgagcagttc ccaaccatga tggaggacca     180
cttcggcggt tcccagcgtg ctggtgtcat tgcagcagca tcaggtttga ccactgcaat     240
cggtaccggg aactccaatg ccggtctgaa cggctggtac ctctcgatgc tcatgcacaa     300
ggaaggatgg tcacgtctcg gtttcttcgg ctacgacctg caggaccagt gtggttcagc     360
aaactcgatg tcgatcagac cggatgaagg tctcctcggt gaactccgtg gacca          415
```

<210> SEQ ID NO 16
<211> LENGTH: 415
<212> TYPE: DNA
<213> ORGANISM: Unknown
<220> FEATURE:
<223> OTHER INFORMATION: uncultured archaeon

<400> SEQUENCE: 16

```
tgcatacacc gacaacatcc ttgatgacta cacccagtac ggtctggact atatcaagaa      60
gaaacacggt ggcctcgcaa aggcaaaggc gacccaggaa gtcgtcagcg acatcgcaac     120
cgaggtcaac ctctacggta tggagcagta cgaaacctac ccaaccgctc tcgagagcca     180
cttcggtgga tcccagcgtg catccgtcct tgcagcagca tccggtatca ccacttcact     240
ggctaccgca aactccaacg cgggcctgaa cggctggtac ttgtccatgc tcatgcacaa     300
```

```
ggaaggctgg tcacgtctcg ggttcttcgg ctacgacctg caggaccagt gtggttccgc    360
aaactccatg tcgatccgtc ccgacgaggg attactcggc gagctccgtg gaccg         415
```

<210> SEQ ID NO 17
<211> LENGTH: 415
<212> TYPE: DNA
<213> ORGANISM: Unknown
<220> FEATURE:
<223> OTHER INFORMATION: uncultured archaeon

<400> SEQUENCE: 17

```
agcctacacc aacgatgtcc tggacgactt ctgctactac ggcgtcgact tcgccgcaga    60
taagttcgga ggattcgcca agtcacccaa gactctggac atcgccaagg agctggccac   120
tgaggtcaac gcctacggca tggagcagta cgaggaattc ccgactctgc tcaggatca    180 cttcggtgga tcccagagag catccgttct ggcagccgca tccggtatca cttccgccat   240
cgcctctggc cacagccagg taggccttgc cggatggtac ctgtctatgc tcctgcacaa   300
ggaaggctgg ggacgcctgg gcttcttcgg ctacgacctg caggatcaat gcggtccaac   360
caacgtgttc tcctaccagt ccgacgaggg cgcacccctc gagctgaggg gagct       415
```

<210> SEQ ID NO 18
<211> LENGTH: 435
<212> TYPE: DNA
<213> ORGANISM: Unknown
<220> FEATURE:
<223> OTHER INFORMATION: uncultured archaeon

<400> SEQUENCE: 18

```
tgcatacacc gatgatatcc tcgacaacaa catctactac gacgttgact acatcaacga    60
caagtacaac ggtgcagcaa ccatcggcaa ggacaacaag ttaaaggcaa gcctcgaaat   120
cgtaaaggac attgcaaccg agtccacaat ctacggtatg gagacctacg agaagttccc   180
aaccgctctt gaagaccact tcggtggatc ccagagagca accgtgctcg cagctgcagc   240
tggtgttgca tgcgccctcg gaactgcaaa cgccaacgct ggtctctccg gctggtacct   300
ctccatgtac ctgcacaagg aagcatgggg ccgtctcggt tcttcggata cgaccttgca   360
ggaccagtgc ggtgccacaa acgtttctgt cctaccaggg cgacgaaggt ctcccagacg   420
aactccgtgg tccca                                                    435
```

<210> SEQ ID NO 19
<211> LENGTH: 367
<212> TYPE: DNA
<213> ORGANISM: Unknown
<220> FEATURE:
<223> OTHER INFORMATION: uncultured archaeon

<400> SEQUENCE: 19

```
tctacgtcaa gagaaacatg gtggcatcgc aaaggcaaag gcgacacagg aagttgtcag    60
cgacatcgca accgaggtca acctctacgg tatggagcag tacgagacct acccgaccgc   120
cctcgagagc cacttcggcg gatcccagcg tgcatccgtc cttgcagcag catcaggtat   180
ttcctgtgca atggcaacgg caaactccaa cgccggtctg aacggctggt acctgtcgat   240
gctcatgcac aaggaaggct ggtcacgtct cggtttcttc ggctacgacc tgcaggacca   300
gtgcggttcc gcaaactcca tgtcaatccg tccagcgag ggattactcg gagaactccg   360
tggaccg                                                             367
```

```
<210> SEQ ID NO 20
<211> LENGTH: 415
<212> TYPE: DNA
<213> ORGANISM: Unknown
<220> FEATURE:
<223> OTHER INFORMATION: uncultured archaeon

<400> SEQUENCE: 20
tgcatacacc aacgatgtcc tggacgactt ctgctactac ggcgtcgact tcgccgcaga      60
caagttcggt ggattcgcca aggcacccaa gaccctggat atcgccaagg aattggcaac     120
cgaggtcaac gcttatggtg ttgagcagta cgaggcattc ccgactctgc tcgaggatca     180
cttcggtgga tcccagaggg catccgtcct cgcagccgca tccggtatca cctcagccat     240
cgcctccggc cacagccagg tcggtctcgc cggctggtac ctgagcatgc tcctgcacaa     300
ggaatcctgg ggacgcttgg gcttcttcgg ctacgacttg caggatcaat gcggtccaac     360
caacgtattc tcctaccagt cagacgaggg caaccccgtc gagctgaggg gcgca          415

<210> SEQ ID NO 21
<211> LENGTH: 18
<212> TYPE: DNA
<213> ORGANISM: Artificial Sequence
<220> FEATURE:
<223> OTHER INFORMATION: Synthetic Construct

<400> SEQUENCE: 21
gcggttttct aggttgtc                                                    18

<210> SEQ ID NO 22
<211> LENGTH: 18
<212> TYPE: DNA
<213> ORGANISM: Artificial Sequence
<220> FEATURE:
<223> OTHER INFORMATION: Synthetic Construct

<400> SEQUENCE: 22
caccttgctg atatgcgg                                                    18
```